(12) United States Patent
Holmqvist (10) Patent No.: US 9,132,235 B2
(45) Date of Patent: Sep. 15, 2015

(54) MEDICAMENT DELIVERY DEVICE

(75) Inventor: Anders Holmqvist, Värmdö (SE)

(73) Assignee: SHL Group AB, Nacka Strand (SE)

(*) Notice: Subject to any disclaimer, the term of this patent is extended or adjusted under 35 U.S.C. 154(b) by 211 days.

(21) Appl. No.: 13/885,887

(22) PCT Filed: Nov. 18, 2011

(86) PCT No.: PCT/SE2011/051391
§ 371 (c)(1),
(2), (4) Date: May 17, 2013

(87) PCT Pub. No.: WO2012/067583
PCT Pub. Date: May 24, 2012

(65) Prior Publication Data
US 2013/0237905 A1    Sep. 12, 2013

Related U.S. Application Data

(60) Provisional application No. 61/415,070, filed on Nov. 18, 2010.

(30) Foreign Application Priority Data

Nov. 18, 2010 (SE) ...................... 1051212

(51) Int. Cl.
*A61M 37/00* (2006.01)
*A61M 5/19* (2006.01)
*A61M 5/315* (2006.01)

(52) U.S. Cl.
CPC ............. *A61M 5/19* (2013.01); *A61M 5/31525* (2013.01); *A61M 5/3155* (2013.01)

(58) Field of Classification Search
CPC . A61M 5/19; A61M 5/31525; A61M 5/3155; A61M 5/2066; A61M 2005/2073; A61M 2005/31598; A61M 5/31596
See application file for complete search history.

(56) References Cited

U.S. PATENT DOCUMENTS 8,276,583 B2    10/2012   Farieta et al.
2005/0049551 A1*  3/2005   Kirchhofer .................... 604/82
(Continued)

FOREIGN PATENT DOCUMENTS

GB    2437924 A    11/2007
WO   03/077968 A2   9/2003
(Continued)

OTHER PUBLICATIONS

Sweden Patent Office, Int'l Search Report in PCT/SE2011/051391, Mar. 5, 2012.

(Continued)

*Primary Examiner* — Rebecca E Eisenberg
(74) *Attorney, Agent, or Firm* — Piedmot Intellectual Property (57) ABSTRACT

A medicament delivery device includes a housing arranged to receive a medicament container, a drive unit arranged to act on a stopper in the medicament container, which drive unit includes a torsion drive spring. A dose setting member is operably connected to the drive unit such that a manual turning of the dose setting member causes a tensioning of the torsion drive spring. The device also includes an activation mechanism having an activation button protruding through a distal end of the device. The activation mechanism is operably connected to the drive unit such that actuation of the activation mechanism causes a release of the drive unit, with a set dose of medicament delivered.

19 Claims, 13 Drawing Sheets

(56) References Cited

U.S. PATENT DOCUMENTS

| | | |
|---|---|---|
| 2009/0292240 A1* | 11/2009 | KraMer et al. .................. 604/82 |
| 2010/0065049 A1* | 3/2010 | Farieta et al. ............ 128/203.15 |
| 2010/0094214 A1 | 4/2010 | Abry et al. |
| 2011/0224622 A1 | 9/2011 | Karlsson |
| 2011/0251553 A1* | 10/2011 | Ratjen et al. .................... 604/89 |
| 2012/0029443 A1 | 2/2012 | Holmqvist |

FOREIGN PATENT DOCUMENTS

| | | |
|---|---|---|
| WO | 2010/081489 A1 | 7/2010 |
| WO | 2010/139675 A1 | 12/2010 |
| WO | 2011/101349 A1 | 8/2011 |
| WO | 2011/101351 A1 | 8/2011 |
| WO | 2012/067582 A1 | 5/2012 |
| WO | 2012/067584 A1 | 5/2012 |

OTHER PUBLICATIONS

Sweden Patent Office, Written Opinion in PCT/SE2011/051391, Mar. 5, 2012.

Sweden Patent Office, Int'l Preliminary Report on Patentability in PCT/SE2011/051391, Mar. 19, 2013.

* cited by examiner

MEDICAMENT DELIVERY DEVICE

TECHNICAL AREA

The present invention relates to a medicament delivery device and in particular a medicament delivery device utilizing multi-chamber medicament containers that require mixing before drug delivery to a patient.

BACKGROUND OF INVENTION

It is becoming more and more common to use multi-chamber medicament containers in medicament delivery devices such as injectors. The reason for this is that the medicament can be stored for much longer time periods without being degraded in comparison with medicament dissolved in some liquid.

Thus the medicament and the liquid are kept in different compartments in the medicament container and are mixed just before use by moving a dividing wall or stopper such that the compartments can communicate with each other.

However, the multi-chamber medicament containers entail more handling steps before a dose of medicament can be injected in that the plunger rod of the injector has to move the stopper or stoppers of the medicament container in order to initiate the mixing.

Another feature of many medicament delivery devices and in particular injectors is the attachment of a medicament delivery member, in particular an injection needle to a medicament container and then how to avoid unintentional needle sticks. Document WO2010/000559 discloses a medicament delivery device utilizing a multi-chamber medicament container where the mixing is obtained by rotating a medicament container holder, positioned in the proximal housing part, into a distal housing part whereby the stopper of the medicament container is moved against a plunger rod. In the initial position the proximal end of the medicament container is protruding beyond the proximal housing part, where the latter also acts as a needle shield, such that a medicament delivery device can be attached to the medicament container holder. When the mixing has been performed, the medicament delivery member is drawn into the proximal housing/needle shield. The needle shield is now used for actuating the device in that when a penetration is performed, the needle shield is pushed in the distal direction, whereby it triggers an auto-injection sequence. Thus the needle shield assembly extends almost to the distal end of the device in order to be able to actuate the injection.

However, for some devices it is neither necessary nor desirable to have so many components and functions since they tend to make the devices more complex and more expensive. Also the holding of the device during mixing may be performed with one hand rather close to the proximal end of the device instead of the distal end of the device. There is thus room for development of medicament delivery devices.

BRIEF DESCRIPTION OF INVENTION

The aim of the present invention is to provide a medicament delivery device that can handle multi-chamber medicament containers in a simple and intuitive but yet safe way.

According to a main aspect of the invention it is characterised by a medicament delivery device according to the features of the independent patent claim. Preferable embodiments of the invention form the subject of the dependent patent claims.

According to a main aspect of the invention it is characterised by a medicament delivery device comprising a body which comprises a housing and a medicament container holder accommodating a multi-chamber medicament container, wherein said housing and said medicament container holder are interactively connected to and movable relative each other; the medicament container holder comprising attachment means for attaching a delivery member; a mixing guard mechanism interactively connected to the body for driving the medicament container holder within the housing and thereby achieving a reconstitution wherein the mixing guard mechanism comprises a mixing cylinder unit and a tubular medicament delivery member guard operably connected to the medicament container holder, such that when the mixing cylinder unit is operated, the medicament container holder is moved in relation to the medicament delivery member guard between a pre-mix position in which said attachment means protrudes through a proximal end of said medicament delivery member guard for allowing the attachment of a delivery member and a mixed position in which said attachment means and said attached delivery member is positioned within the medicament delivery member guard, wherein said mixing guard mechanism further comprises a guard lock and release member operably connected to said guard and to said medicament container holder, such that said guard lock and release member is configured to lock said guard when the container holder is in the pre-mix position and to release said guard when the container holder is moved to the mixed position.

According to another aspect of the invention movement in the distal direction of the guard member, when the device is pressed against a dose delivery site, causes a turning of a rotator member comprised in said mixing cylinder unit.

According to further aspect of the invention said turning is caused by said rotator member comprising at least one groove inclined in relation to the longitudinal direction of the device, cooperating with at least one protrusion arranged on the guard during distal movement of said guard.

According to yet another aspect of the invention said mixing guard mechanism further comprises a resilient member operably arranged to said guard for urging said guard in the proximal direction.

According to yet a further aspect of the invention the rotator member comprises a first guard locking means interactively connected to the rotator member such that proximal movement of said guard, after removal from a medicament delivery site, causes a locking of said guard in a proximal position covering said medicament delivery member.

According to another aspect of the invention said mixing guard mechanism comprises first connection means, interactively connecting said housing and said medicament container holder for allowing the medicament container holder to be displaced within the housing.

According to a further aspect of the invention said first connection means comprises cooperating threads on said housing and said medicament container holder.

According to yet another aspect of the invention said first guard locking means comprises at least one proximally directed resilient tongue arranged to said rotator member and at least one protrusion arranged to said guard such that when said guard is proximally displaced, said at least one protrusion passes said at least one tongue, thereby preventing subsequent distal displacement of said guard.

According to yet a further aspect of the invention said medicament container holder and said guard are slidably connected but rotationally locked to each other by second connection means.

According to another aspect of the invention said mixing cylinder is arranged to said guard such that they are slidably connected but rotationally locked to each other by third connection means.

According to a still further aspect of the invention said mixing cylinder and a connector sleeve are fixedly connected to each other by fourth connection means.

According to yet another aspect of the invention said connector sleeve and said housing are connected to each other by fifth connection means which prevent a longitudinal movement in relation to each other but allow rotation in relation to each other.

According to a further aspect of the invention said rotator member and said connector sleeve are connected to each other by sixth connection means which prevent a longitudinal movement in relation to each other but allow partial rotation in relation to each other, and wherein said connector sleeve and said rotator member are coaxially arranged within said mixing cylinder.

According to yet a further aspect of the invention said rotator member and said mixing cylinder are one-directionrotatably connected to each other by seventh connection means.

According to another aspect of the invention it further comprises drive means arranged within said housing and adapted to drive a stopper positioned within said multi-chamber container.

According to yet another aspect of the invention said drive means comprises a plunger rod and a force member operatively acting on said plunger rod for urging it in the proximal direction.

According to a further aspect of the invention it further comprises a holding means for holding said drive means in a pre-tensioned state.

According to yet a further aspect of the invention it comprises activation means capable of acting on said holding means for releasing the drive means from the pre-tensioned state According to another aspect of the invention the device is an injection device.

There are several advantages with the present invention. The use of a tubular medicament delivery member guard operatively connected to the medicament container holder and the mixing means provides the possibility of attaching a medicament delivery member to the device and then during the mixing operation cover the medicament delivery member by activating the tubular guard member. By using a rotator member, several functions of the device are obtained with few components and provides the interaction of functions.

Further the mixing guard mechanism enables a pushing of the tubular guard in the distal direction when the device is pressed against a dose delivery site. This movement of the tubular guard causes components of the mixing guard mechanism to be moved and thus prepared for a locking of the tubular guard member when the device is removed from the dose delivery site after completed dose delivery, wherein the tubular guard is pushed in the proximal direction by the spring force, thereby surrounding the medicament delivery member in a locked state, whereby the medicament delivery member cannot be tampered with.

These and other aspects of, and advantages with, the present invention will become apparent from the following detailed description of the invention and from the accompanying drawings.

BRIEF DESCRIPTION OF DRAWINGS

In the following detailed description of the invention, reference will be made to the accompanying drawings, of which

DETAILED DESCRIPTION OF THE INVENTION

In the present application, when the term "distal part/end" is used, this refers to the part/end of the delivery device, or the parts/ends of the members thereof, which is/are located the furthest away from the medicament delivery site. Correspondingly, when the term "proximal part/end" is used, this refers to the part/end of the delivery device, or the parts/ends of the members thereof, which is/are located closest to the medicament delivery site.

Figure 3:
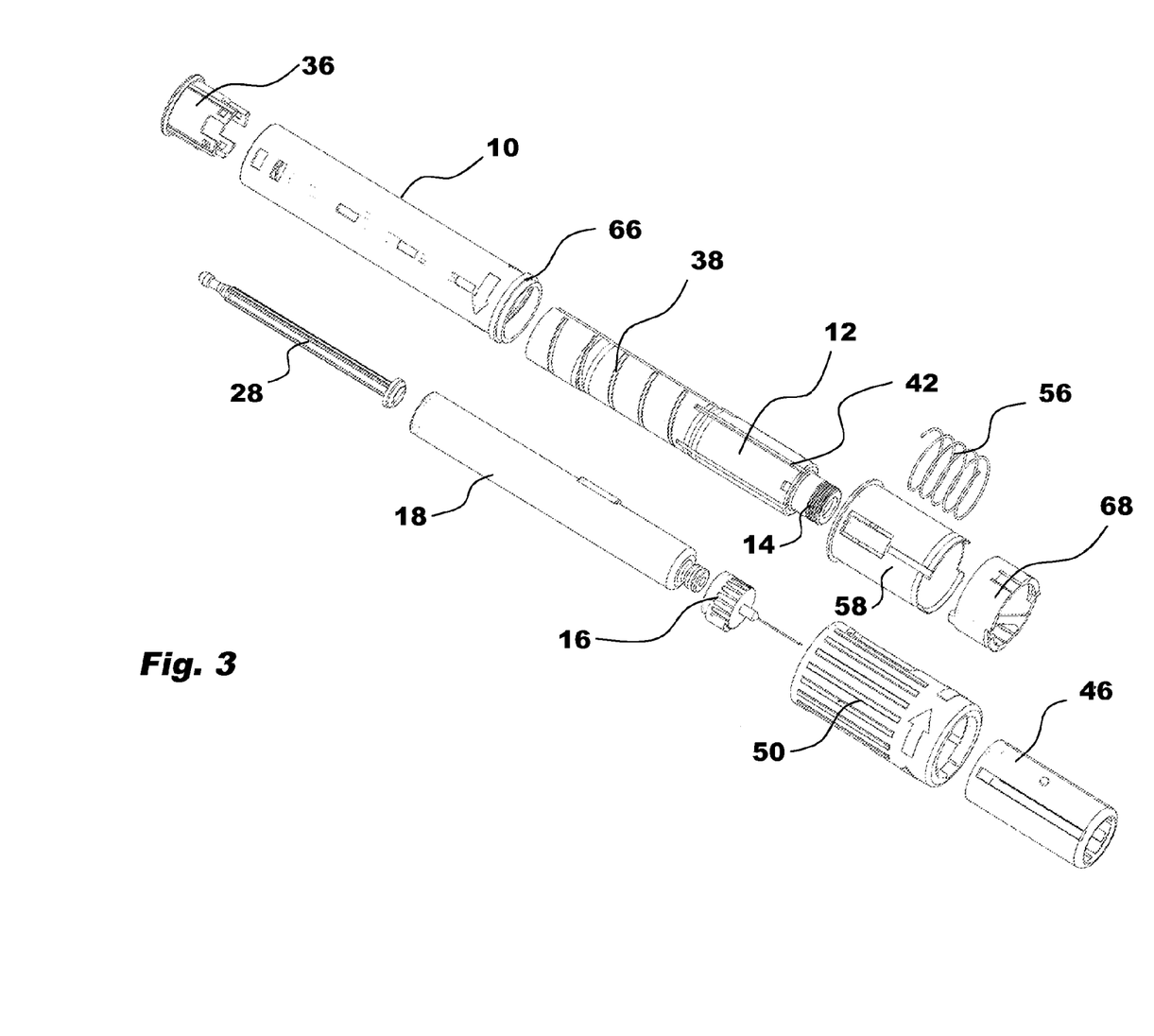
FIG. 3 is an exploded view of the device of FIG. 1.

The medicament delivery device shown in the drawings comprises a body, which in turn comprises a generally elongated housing 10 and a generally tubular medicament container holder 12, FIG. 3. The proximal end of the medicament container holder comprises a neck portion 14 onto which a medicament delivery member 16 may be releasably attached. The interior of the medicament container holder is arranged to house a multi-chamber medicament container 18, having a proximal end fitting into the neck portion 14 of the medicament container holder 12. The interior of the medicament container 12 contains a number of movable stoppers 20, 22, which stoppers form a number of chambers 24, 26 containing medicament in powder form and a diluent.

Figure 1:
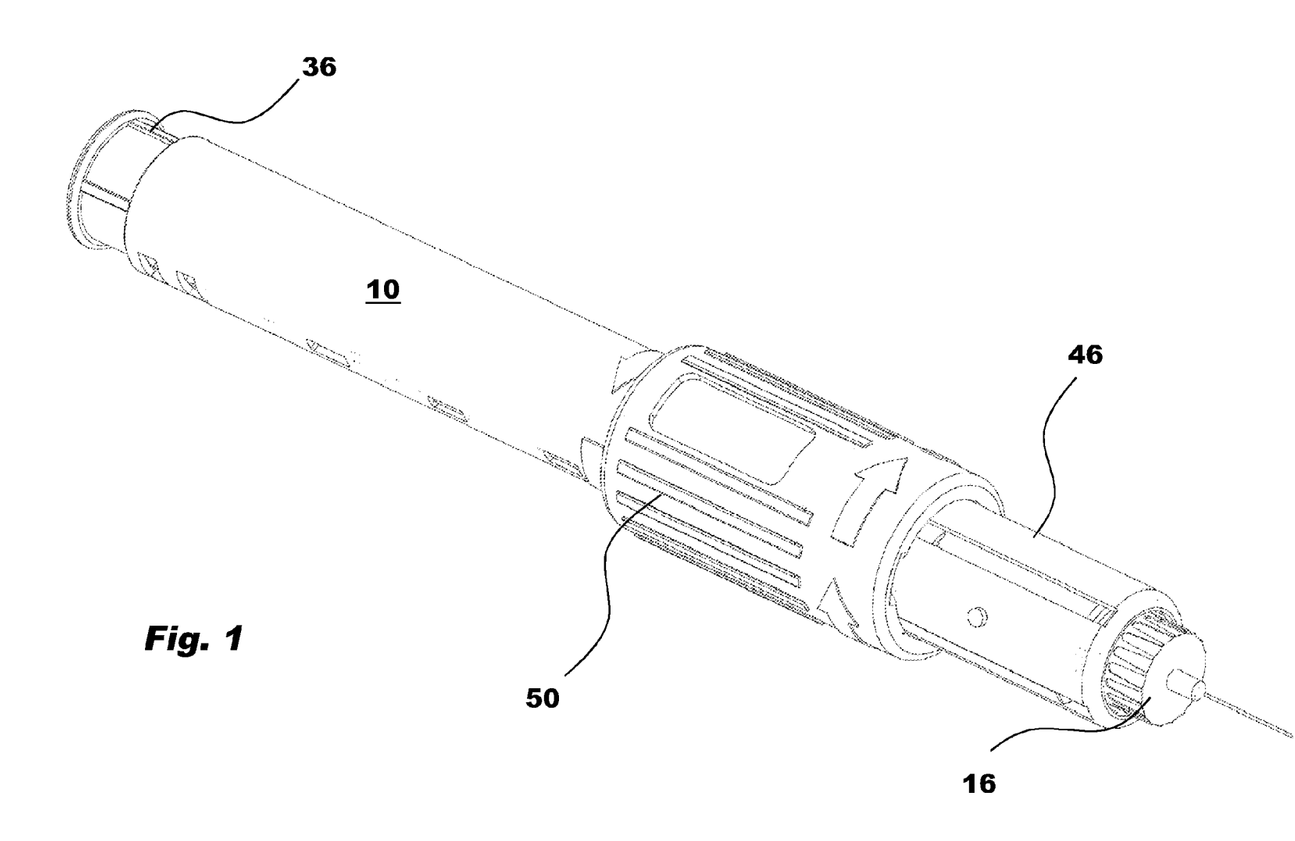
FIG. 1 is a perspective view of a medicament delivery device according to the present invention.
Figure 2:
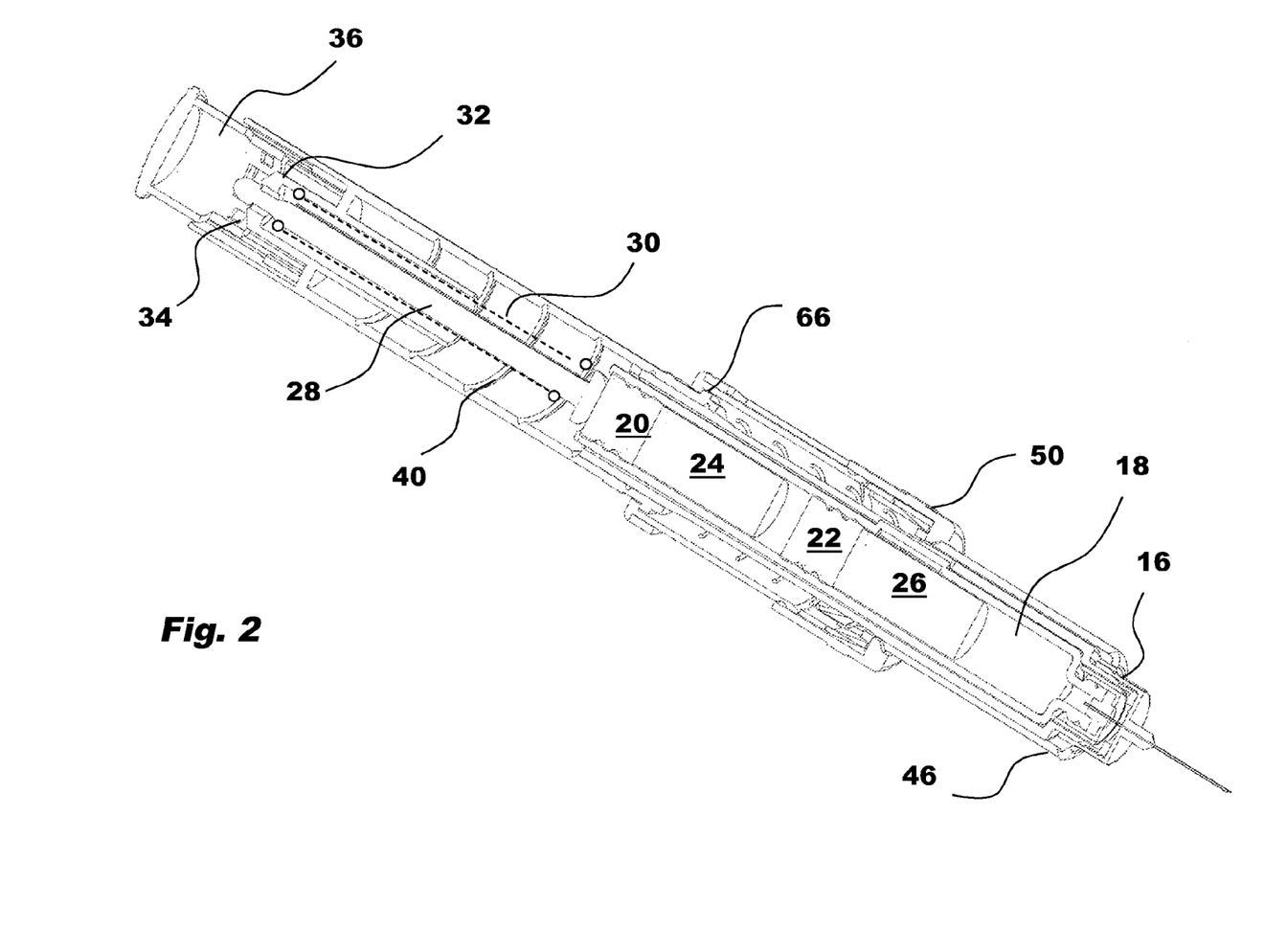
FIG. 2 is a cross-sectional view in perspective of the device of FIG. 1.

A drive mechanism is further arranged in the housing, comprising an elongated plunger rod 28 having a proximal end in contact with the stopper 20 at the distal end of the medicament container 12. The plunger rod 28 is operatively connected to a drive force member 30 of the drive mechanism operatively acting on the plunger rod 28 for urging it in the proximal direction. The device further comprises a holding member 32 capable of holding the drive force member 30 in a pre-tensioned state as well as an actuation member 34 capable of acting on said holding member 32 for releasing the drive force member 30 from the pre-tensioned state, FIG. 2. The actuation member 34 comprises an actuation button 36 extending through a distal end of the housing.

Figure 4:
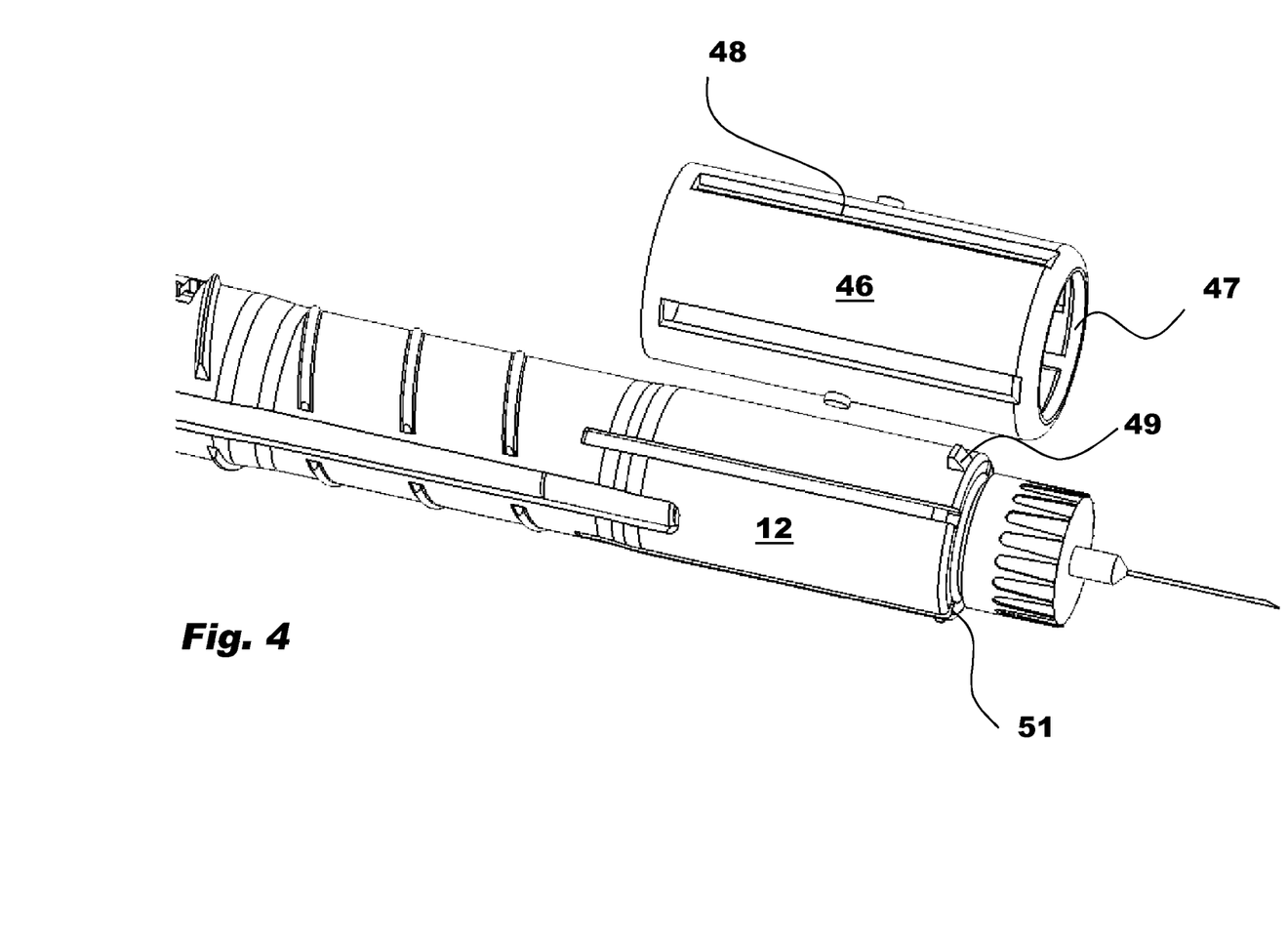
FIG. 4 is a detailed exploded view of a medicament delivery member guard and a proximal housing part.

The device further comprises a mixing guard mechanism arranged for mixing the content of the chambers of the multi-chamber medicament container. Thereby the housing 10 and the medicament container 12 are interactively connected to each other by first connection means for allowing the medicament container holder to be displaced within the housing. The first connection means comprises threads 38 on the outer surface of the medicament container holder 12, which threads 38 cooperate with corresponding threads 40, FIG. 2, on the inner surface of the housing 10. The mixing means further comprises longitudinally extending grooves 42, FIG. 3, on the outer surface of the medicament container holder 12, which grooves 42 cooperate with corresponding ribs 44, FIG. 5, on an inner surface of a generally tubular medicament delivery member guard 46, forming second connection means. Further a guard member lock and release member is arranged wherein the outer surface of the medicament container holder 12 at its proximal end is arranged with two oppositely positioned outwardly directed protrusions 49, FIG. 4. These protrusions 49 are arranged to fit into longitudinal slits or grooves 48 arranged in the medicament delivery member guard 46. The medicament delivery member guard 46 is further arranged with a circumferential ledge 47 around the opening at the proximal end. The ledge is arranged to abut a proximal end surface 51 of the medicament container holder surrounding the neck portion 14, thereby preventing movement of the medicament delivery member guard 46.

Figure 6:
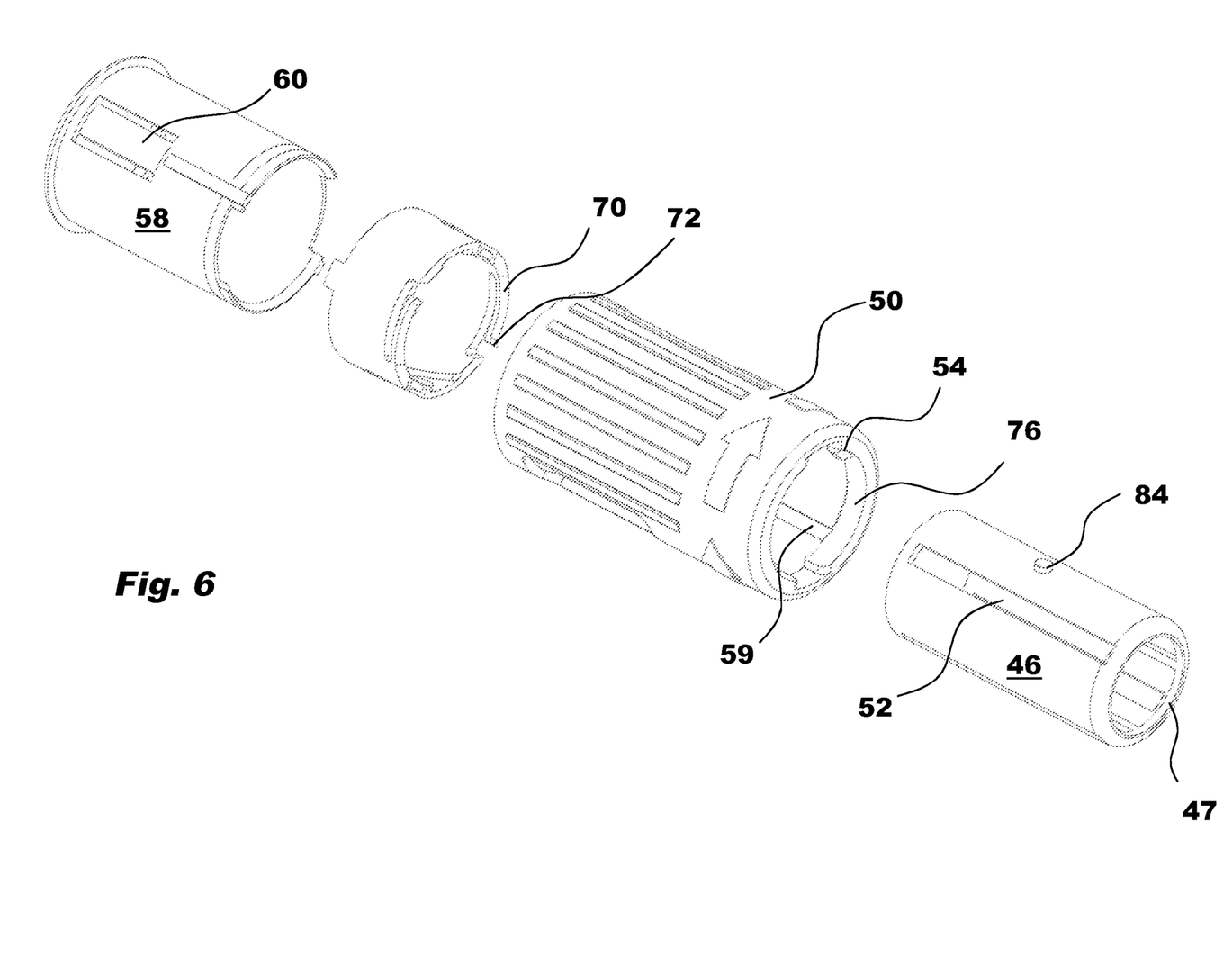
FIG. 6 is the same view as FIG. 4 turned 180°.
Figure 7:
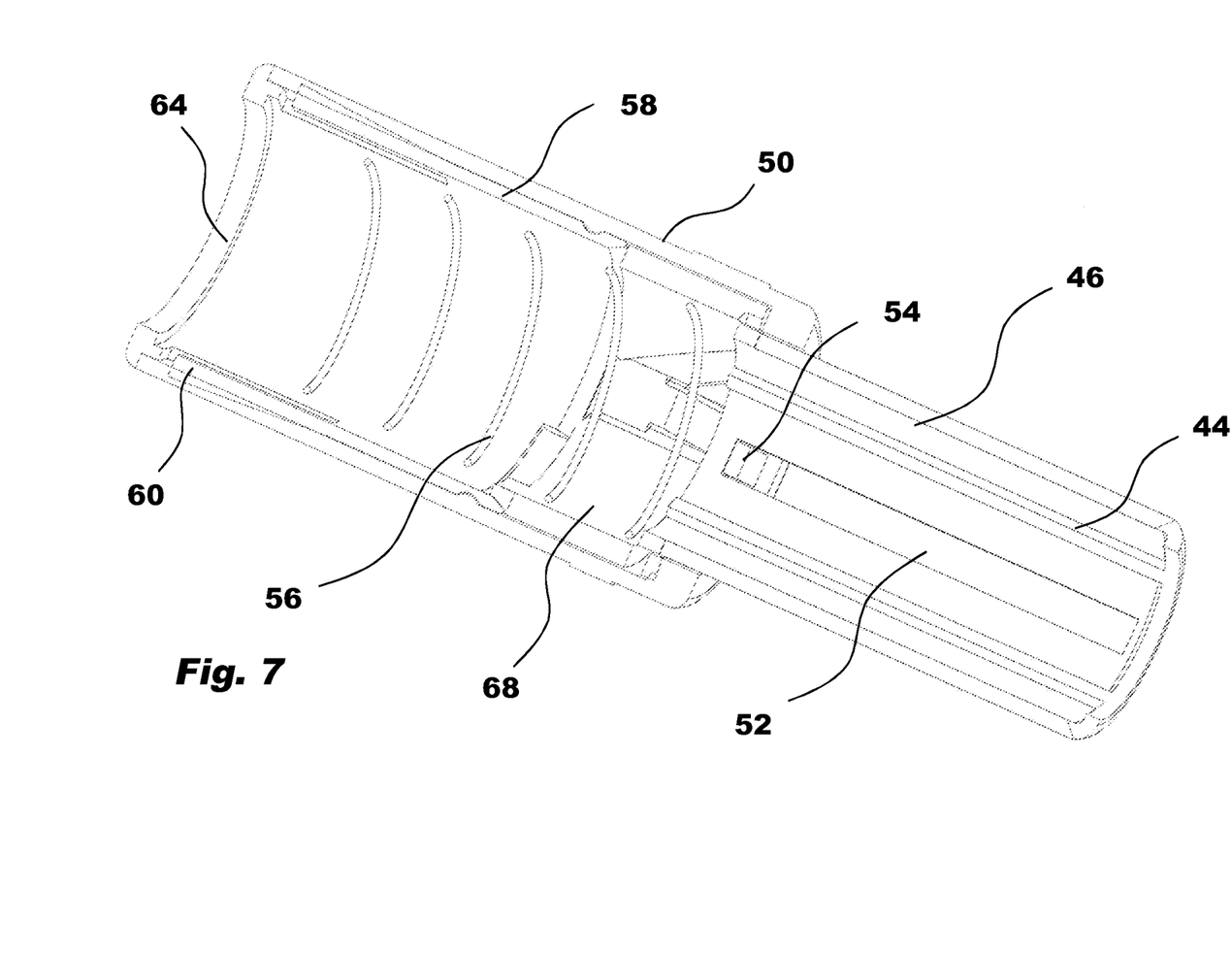
FIG. 7 is a detailed cross-sectional view in of a proximal part of the device of FIG. 1.

Further the medicament delivery member guard 46 is arranged slidable inside a generally tubular mixing cylinder 50 but rotationally locked, via longitudinal grooves 52 on the outer surface of the medicament delivery member guard 46 cooperating with inwardly protruding ledges 54 on the proximal end of the mixing cylinder 50, FIG. 6, forming third connection means. The medicament delivery member guard 46 is urged in the proximal direction in relation to the mixing cylinder 50 by a spring member 56, FIG. 7, acting between a distal end surface of the medicament delivery member guard 46 and a proximal end surface of the housing 10.

Figure 5:
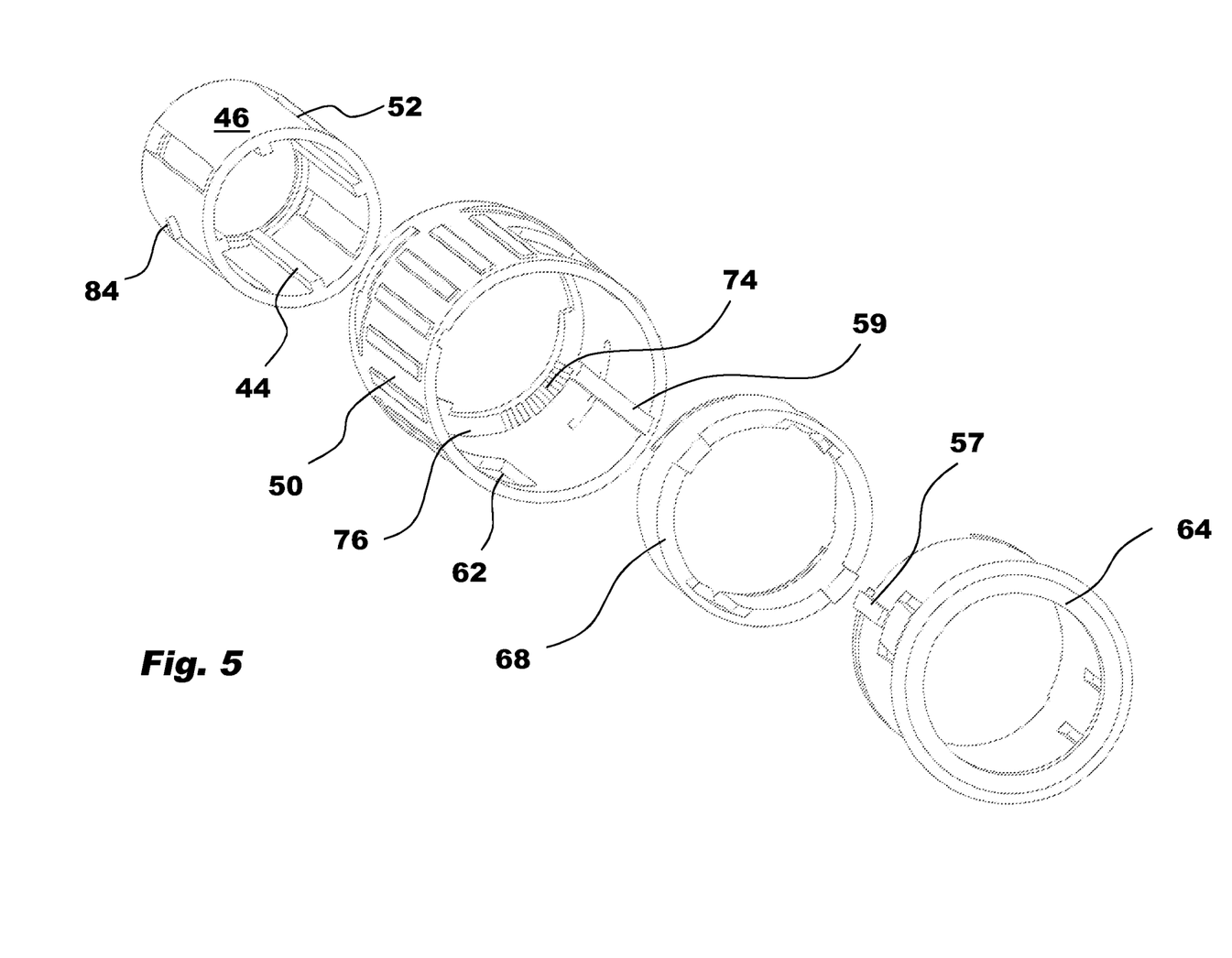
FIG. 5 is a detailed exploded view of key components of the present invention.

Further the mixing cylinder 50 is rotatably attached to the proximal end of the housing 10 via a connector sleeve 58 by a fourth connection means such that it fits into said mixing cylinder 50 and rotationally locked by ribs 57 on the outer surface of the connector sleeve 58 fitting into grooves 59 on the inner surface of the mixing cylinder 50, FIGS. 5, 6. The connector sleeve 58 is attached to the mixing cylinder by outwardly flexible tongues 60 fitting into recesses 62 on the inner surface of the mixing cylinder 50, FIGS. 5 and 6. The connector sleeve 58 is further arranged with a circumferential, inwardly extending ledge 64 in contact with a circumferential ledge 66 of the outer surface of the proximal end of the housing 10, forming a fifth connection means.

Further a generally cylindrical rotator 68 is arranged rotatable inside said mixing cylinder 50 in its proximal end and held in place by the connector sleeve 58 with a sixth connection means. The proximal end surface of the rotator 68 is arranged with flexible tongues 70 extending along the circumference, which are provided with proximally directed wedge-shaped ledges 72, FIG. 8. The ledges 72 cooperate with wedge-shaped ratchets 74 on a distally directed surface of a circumferential ledge 76 of the mixing cylinder 50, such that the rotator 68 can only rotate in one direction in relation to the mixing cylinder 50, forming seventh connection means.

Figure 8:
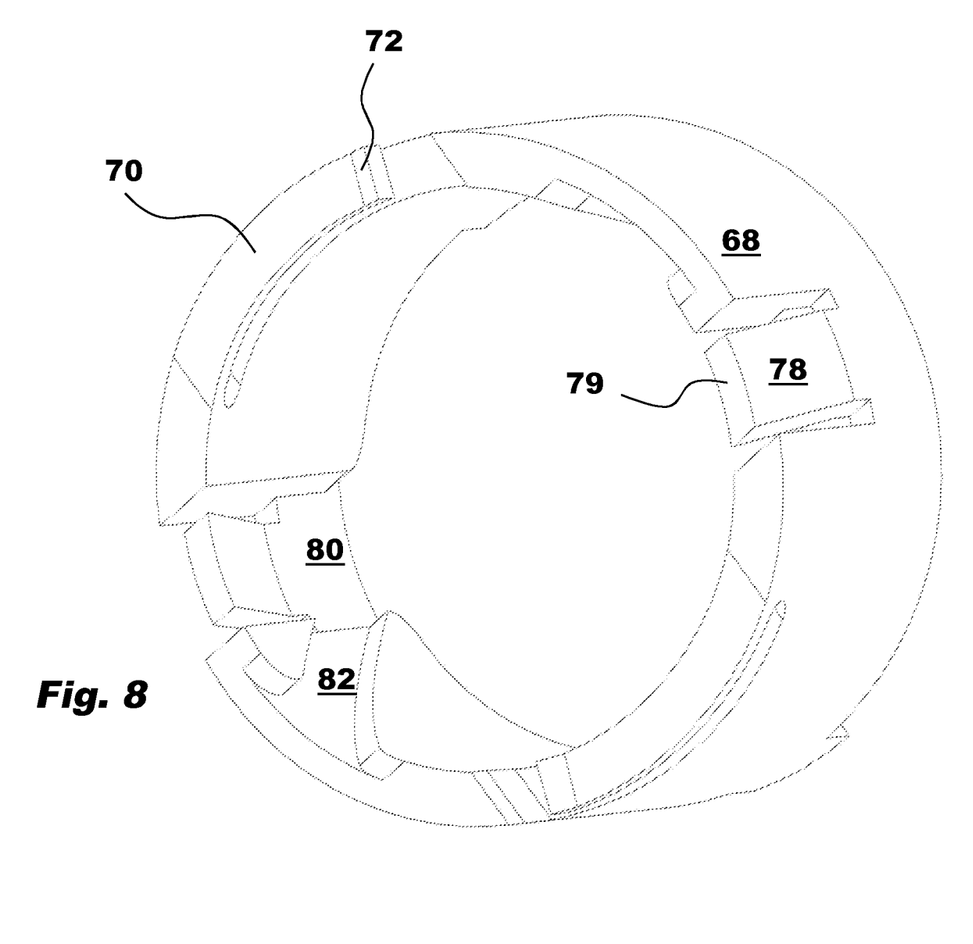
FIG. 8 is a detailed view of a component comprised in the present invention.

The rotator 68 is further arranged with proximally directed, and inwardly flexing, tongues 78 having proximally directed end surfaces 79, FIG. 8, which tongues 78 are arranged in grooves 80 on the inner surface of the rotator 68, which grooves 80 extend in the longitudinal direction of the device, forming eighth connection means. Further the longitudinal grooves 80 are cooperating with inclined grooves 82 that meet at the distal end of the longitudinal grooves 80, the function of which will be described below. Protrusions 84 are further arranged on the outer surface of the medicament delivery member guard 46, which protrusions 84 are arranged to cooperate with the grooves 80, 82 of the rotator 68, as will be described below.

Figure 9:
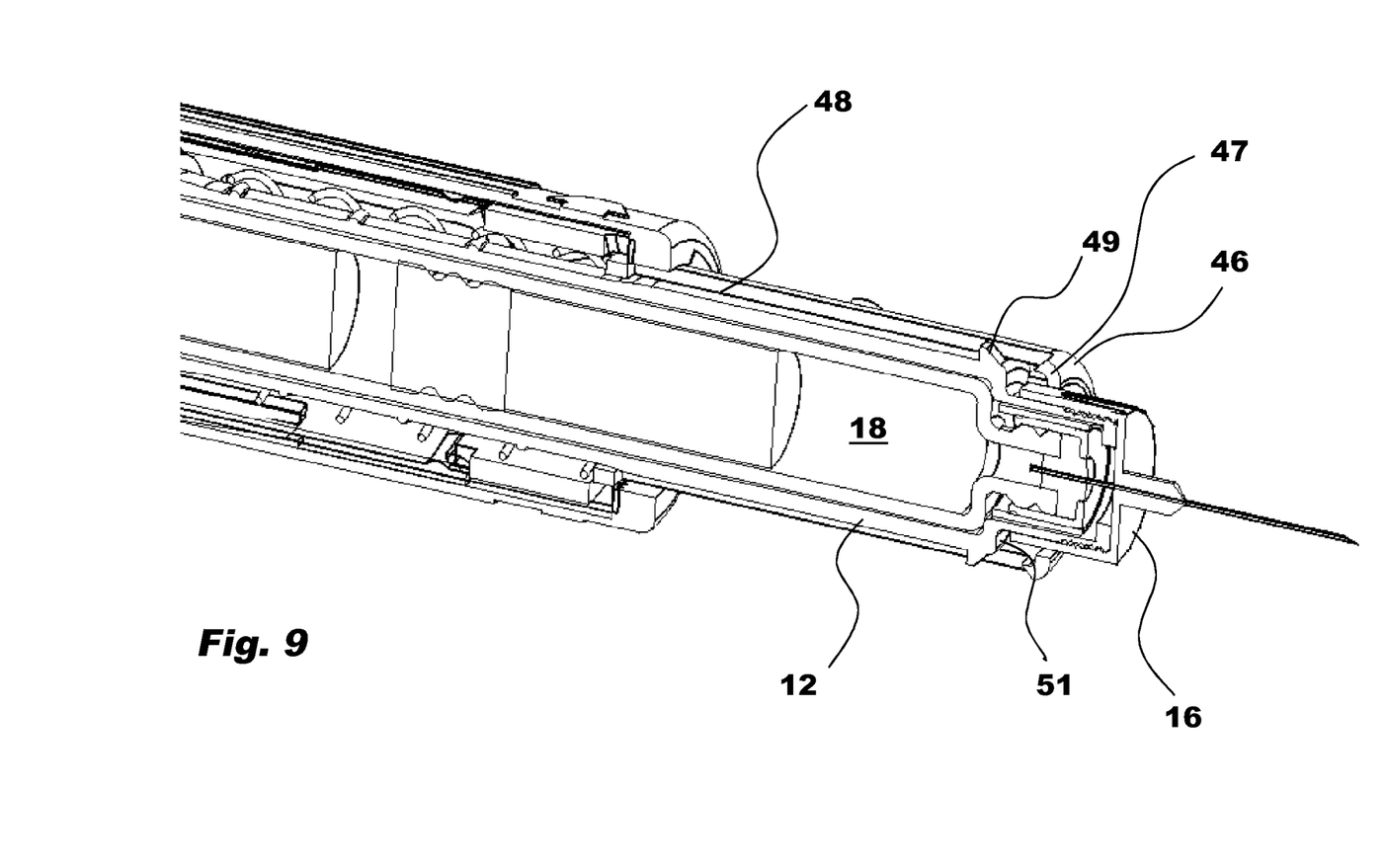
FIGS. 9-13 are cross-sectional views in perspective, partly in detail, displaying different functional states.
Figure 10:
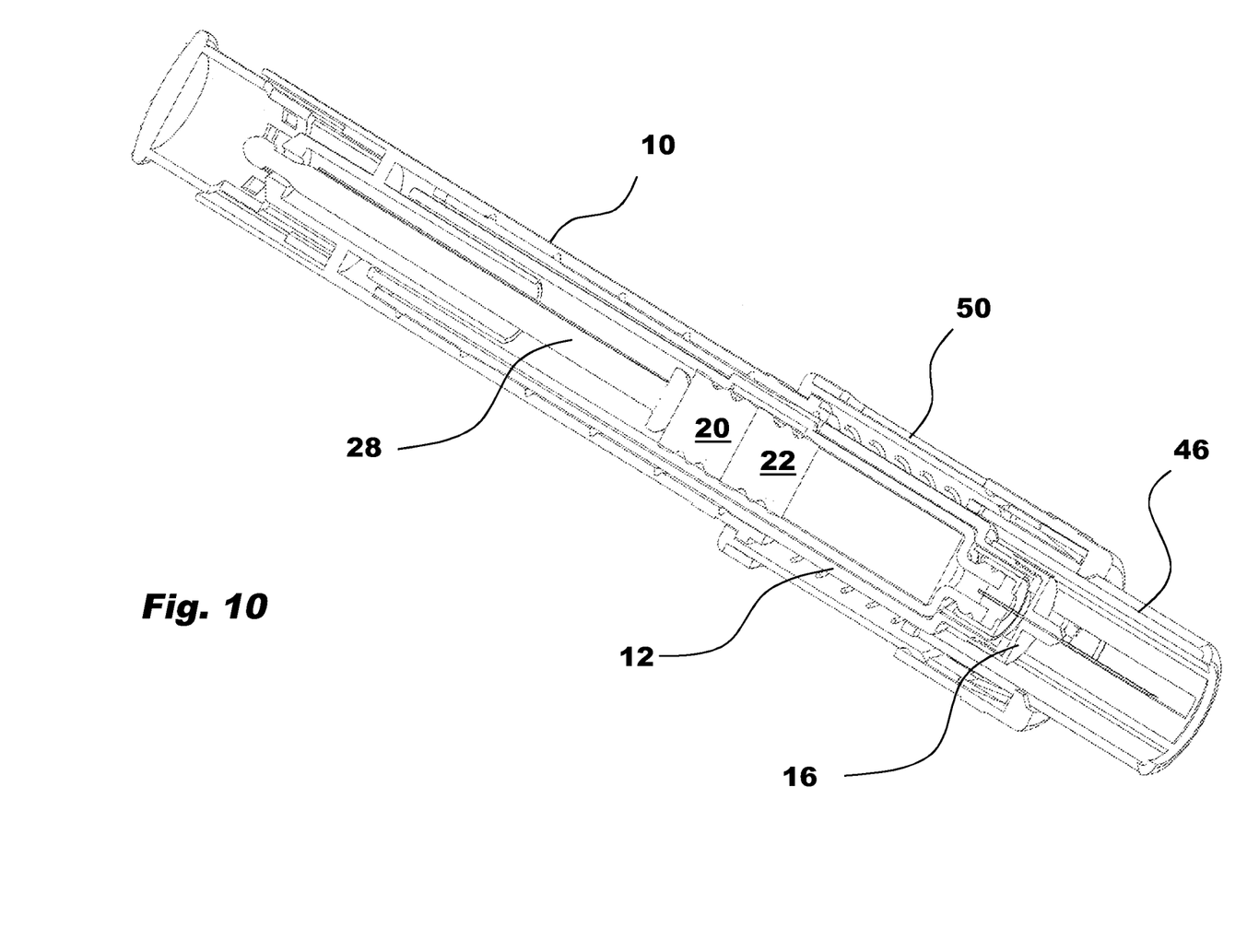
Figure 11:
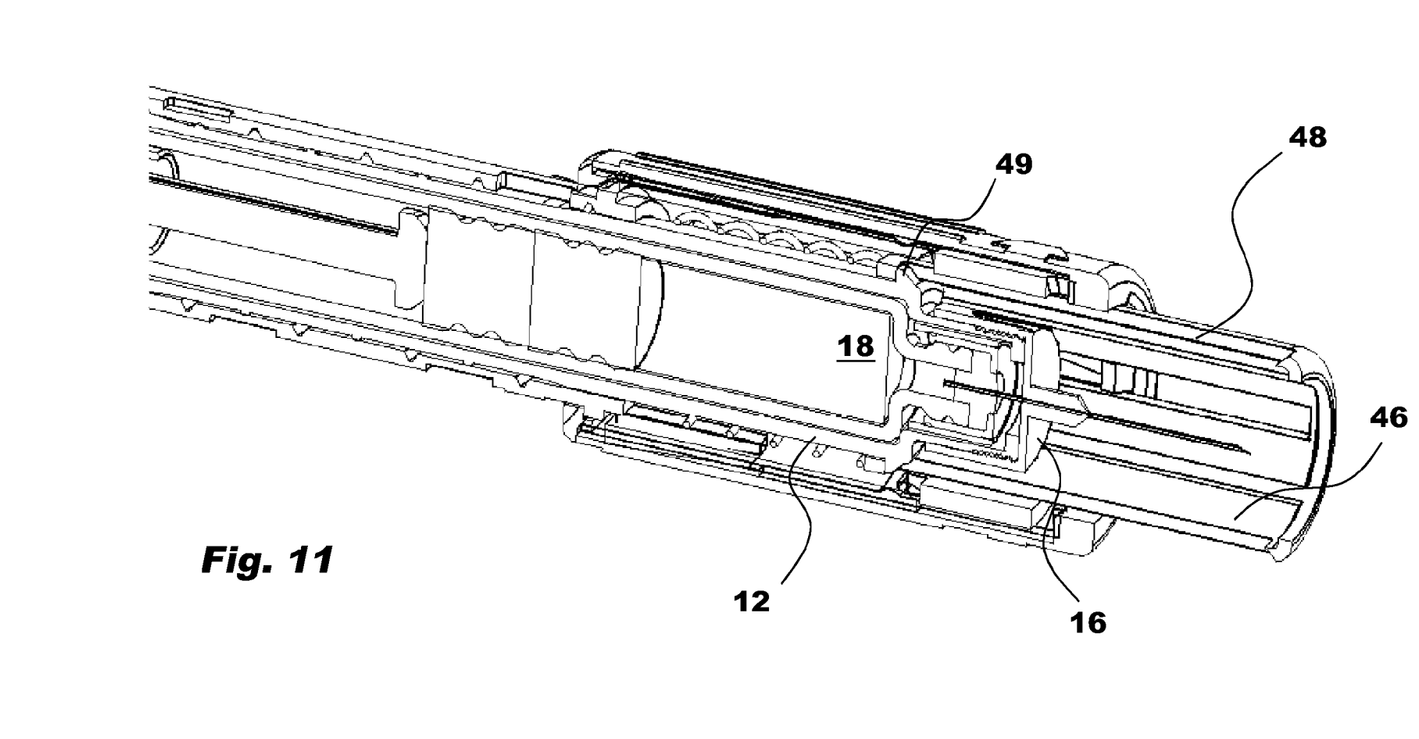

The device is intended to function as follows. When the device is delivered to a user, the proximal end of the medicament container holder 12 protrudes through the proximal end of the medicament delivery member guard 46, FIG. 2. This enables a medicament delivery member 14 to be attached to the proximal end of the medicament container holder 12. In this position the proximal end surface 51 of the medicament container holder 12 is in contact with the circumferential ledge 47 of the medicament delivery member guard 46, whereby the latter is locked against distal movement, FIG. 9. After a medicament delivery member 16 has been attached, the next step is to perform the mixing. This is performed by rotating the mixing cylinder 50 in relation to the housing 10. This causes the medicament container holder 12 to be moved in the distal direction because of the threads 38 of the medicament container holder 12 cooperating with the threads 40 of the housing. The distal movement of the medicament container holder causes the medicament delivery member 14 to be moved into the medicament delivery member guard 46, FIG. 10. The protrusion 49 on the container holder 12 will slide in the groove 48 of the medicament delivery member guard 46 until the container holder and thus the proximal end of the medicament delivery member has reached a certain distance in relation to the proximal end of the guard 46, FIG. 11, which also releases the guard such that it is movable in the longitudinal direction against the force of the spring member 56. In this position the protrusions 49 will come in contact with the distal end of the grooves 48 whereby the guard 46 will also be moved in the distal direction until the mixing sequence has been completed.

The next step is to press the proximal end of the device against the medicament delivery site, such an injection site. The pressing of the device causes the medicament delivery member guard 46 to be pushed in the distal direction into the device and against the force of the medicament delivery member guard spring drive member 56, thereby exposing the medicament delivery member 16. The distance that the container holder 12 and its medicament delivery member 16 have been previously moved distally in relation to the guard, i.e. the length of the groove 48, correspond to a desired and set injection depth when the medicament delivery member is an injection needle.

Figure 12:
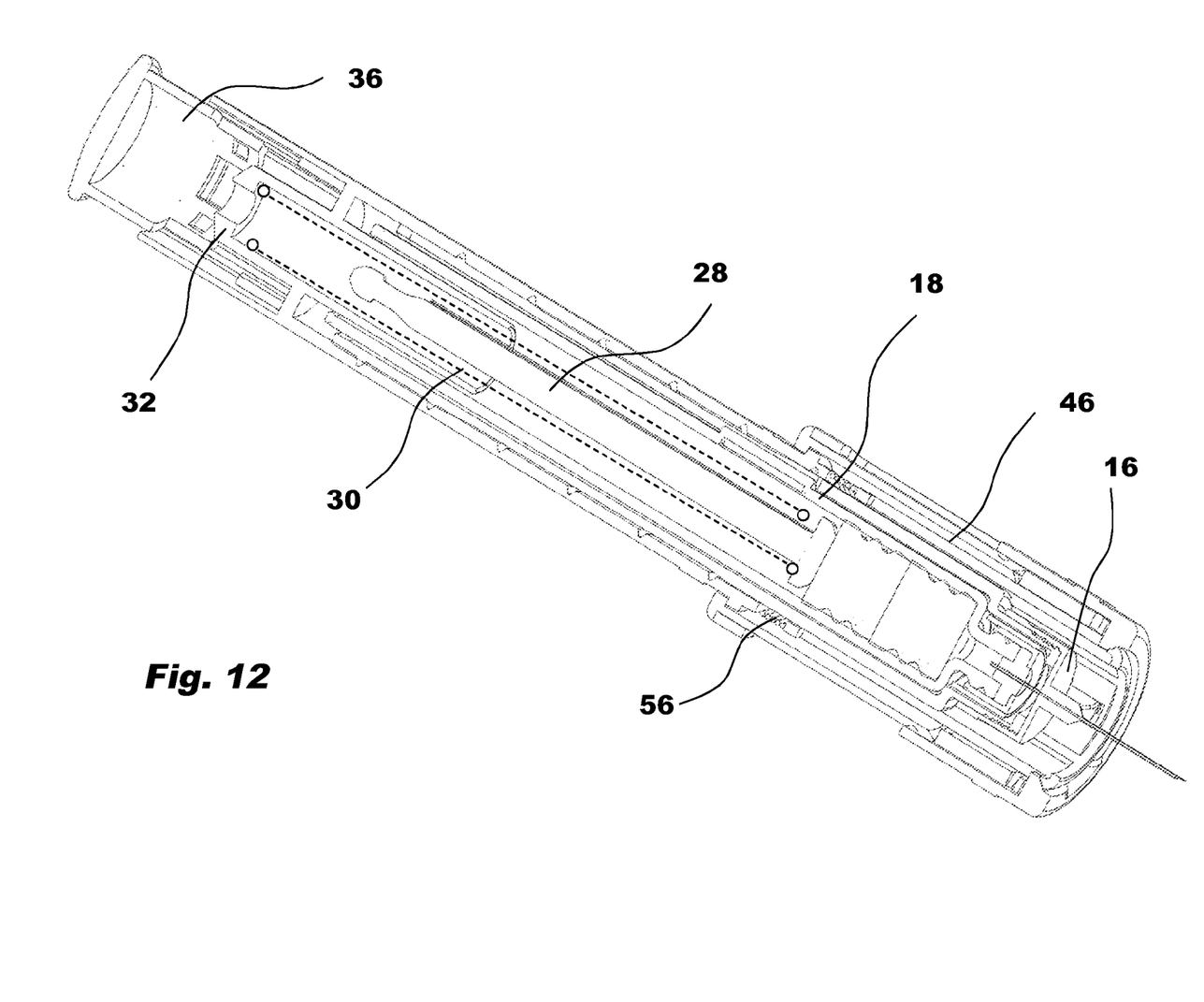

The distal movement of the medicament delivery member guard 46 causes its protrusions 84 to slide along the side surfaces of the inclined grooves 82 whereby the rotator 68 is turned. When the device is fully pressed against the delivery site, the medicament delivery mechanism is activated and a dose of medicament is delivered through the medicament delivery member 16, FIG. 12. Thus, when the actuation button 36 is pressed, the lock member releases the drive member for delivering a dose. However, instead of an automatic dose delivery function, there could instead be a purely manual dose delivery function such that the actuation button acts directly on the plunger rod, whereby the latter is pushed in the proximal direction when the actuation button is pressed. Also, the device may be provided with some kind of actuation locking and release means which acts to keep the actuation mechanism locked until a mixing operation is completed, in order to avoid unintentional activation until the device is ready for use.

Figure 13:
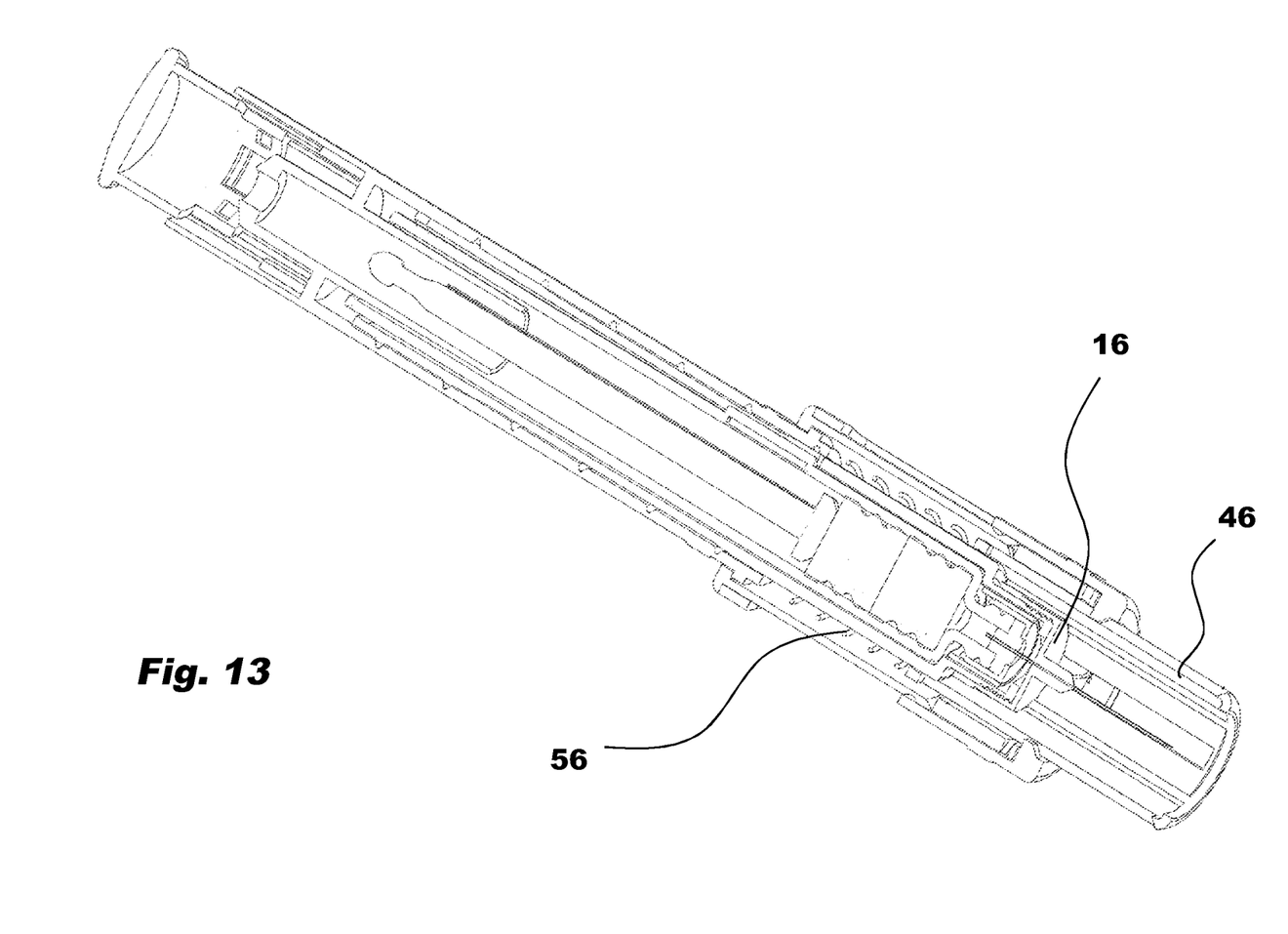

When a dose of medicament has been delivered, the device may be withdrawn from the site. This causes the medicament delivery member guard 46 to be again pushed in the proximal direction, whereby its protrusions 84 slide along the longitudinally directed grooves 80 of the rotator 68 until the protrusions 82 slide over and pass the tongues 78, after which the medicament delivery member guard 46 is covering the medicament delivery member. This will lock the medicament delivery member guard 46 against being pushed again in the distal direction in that its protrusions 84 will come in contact with the proximal end surfaces 79 of the tongues 78, which, in the case when the medicament delivery member is an injection needle, prevents unintentional needle sticks, FIG. 13. The device may now be discarded.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
a body, comprising a housing and a medicament container holder configured for accommodating a multi-chamber medicament container, wherein the housing and medicament container holder are interactively connected to and movable relative each other, and the medicament container holder comprises an attachment device configured for attaching a delivery member;
a mixing guard mechanism interactively connected to the body for driving the medicament container holder within the housing, thereby achieving a reconstitution; wherein the mixing guard mechanism comprises a mixing cylinder unit and a tubular medicament delivery member guard operably connected to the medicament container holder such that when the mixing cylinder unit is operated, the medicament container holder is moved in relation to the medicament delivery member guard between a pre-mix position, in which the attachment device protrudes through a proximal end of the medicament delivery member guard for allowing attachment of the delivery member, and a mixed position, in which the attachment device and attached delivery member are positioned within the medicament delivery member guard; and the mixing guard mechanism further comprises a guard lock and release member operably connected to the medicament delivery member guard and to the medicament container holder such that the guard lock and release member is configured to lock the medicament delivery member guard when the container holder is in the pre-mix position and to release the medicament delivery member guard when the container holder is moved to the mixed position.

2. The medicament delivery device of claim 1, wherein movement of the guard member in a distal direction when the medicament delivery device is pressed against a dose delivery site causes a turning of a rotator member included in the mixing cylinder unit.

3. The medicament delivery device of claim 2, wherein the turning is caused by the rotator member, and the rotator member includes at least one groove inclined in relation to a longitudinal direction of the medicament delivery device that cooperates with at least one protrusion arranged on the medicament delivery member guard during distal movement of the medicament delivery member guard.

4. The medicament delivery device of claim 2, wherein the rotator member comprises a first guard locking device interactively connected to the rotator member such that proximal movement of the medicament delivery member guard, after removal from a medicament delivery site, causes a locking of the guard in a proximal position covering the medicament delivery member.

5. The medicament delivery device of claim 4, wherein the first guard locking device comprises at least one proximally directed resilient tongue arranged to the rotator member and at least one protrusion arranged to the medicament delivery member guard such that when the medicament delivery member guard is proximally displaced, the at least one protrusion passes the at least one tongue, thereby preventing subsequent distal displacement of the medicament delivery member guard.

6. The medicament delivery device of claim 1, wherein the mixing guard mechanism further comprises a resilient member operably arranged to the medicament delivery member guard for urging the medicament delivery member guard in the proximal direction.

7. The medicament delivery device of claim 1, wherein the mixing guard mechanism comprises a first connection device interactively connecting the housing and the medicament container holder for allowing the medicament container holder to be displaced within the housing.

8. The medicament delivery device of claim 7, wherein the first connection device comprises cooperating threads on the housing and the medicament container holder.

9. The medicament delivery device of claim 1, wherein the medicament container holder and the medicament delivery member guard are slidably connected but rotationally locked to each other by a second connection device.

10. The medicament delivery device of claim 1, wherein the mixing cylinder unit is arranged to the medicament delivery member guard such that they are slidably connected but rotationally locked to each other by a third connection device.

11. The medicament delivery device of claim 10, wherein the mixing cylinder unit and a connector sleeve are fixedly connected to each other by a fourth connection device.

12. The medicament delivery device of claim 11, wherein the connector sleeve and the housing are connected to each other by a fifth connection device that prevents longitudinal movement of the connector sleeve and housing in relation to each other but allows rotation in relation to each other.

13. The medicament delivery device of claim 12, wherein the rotator member and the connector sleeve are connected to each other by a sixth connection device that prevents longitudinal movement of the rotator member and connector sleeve in relation to each other but allows partial rotation in relation to each other, and the connector sleeve and rotator member are coaxially arranged within the mixing cylinder unit.

14. The medicament delivery device of claim 13, wherein the rotator member and the mixing cylinder unit are one-direction-rotatably connected to each other by a seventh connection device.

15. The medicament delivery device of claim 1, further comprising a drive mechanism arranged within the housing and configured to drive a stopper positioned within the multi-chamber medicament container.

16. The medicament delivery device of claim 15, wherein the drive mechanism comprises a plunger rod and a force member operatively acting on the plunger rod for urging the plunger rod in the proximal direction.

17. The medicament delivery device of claim 15, further comprising a holder configured to hold the drive mechanism in a pre-tensioned state.

18. The medicament delivery device of claim 17, wherein further comprising an activation mechanism configured to act on the holder for releasing the drive mechanism from the pre-tensioned state.

19. The medicament delivery device of claim 1, wherein the device is an injection device.

* * * * *